United States Patent [19]

Keshaviah et al.

[11] Patent Number: 5,641,405

[45] Date of Patent: Jun. 24, 1997

[54] METHOD AND APPARATUS FOR PURIFIED PULSE PERITONEAL DIALYSIS USING A SINGLE PUMP

[75] Inventors: Prakash R. Keshaviah, Plymouth; Paul Frederick Emerson, Minnetonka; Jian Ruan, Maplewood, all of Minn.

[73] Assignee: Baxter International Inc., Deerfield, Ill.

[21] Appl. No.: 613,777

[22] Filed: Feb. 28, 1996

Related U.S. Application Data

[63] Continuation of Ser. No. 261,516, Jun. 17, 1994, abandoned.

[51] Int. Cl.$^6$ ............................................. A61M 1/28
[52] U.S. Cl. .................... 210/645; 210/85; 210/86; 210/90; 210/97; 210/195.2; 210/321.65; 210/321.71; 210/646; 210/739; 210/741; 210/805; 210/929; 604/28; 604/29; 604/30; 604/65; 604/67
[58] Field of Search .................... 210/195.1, 85, 210/195.2, 86, 97, 252, 258, 90, 321.65, 321.71, 416.1, 645, 646, 739, 741, 805, 929; 604/4, 28, 29, 30, 53, 65, 67

[56] References Cited

U.S. PATENT DOCUMENTS

| | | | |
|---|---|---|---|
| 4,190,047 | 2/1980 | Jacobsen et al. | 604/29 |
| 4,276,175 | 6/1981 | Bower | 210/646 |
| 4,412,917 | 11/1983 | Ahjopalo | 210/321.65 |
| 4,618,343 | 10/1986 | Polaschegg | 210/646 |
| 4,964,976 | 10/1990 | Lysaght et al. | 210/650 |
| 5,141,493 | 8/1992 | Jacobsen et al. | 604/29 |
| 5,178,763 | 1/1993 | Delaunay | 210/646 |
| 5,438,510 | 8/1995 | Bryant et al. | 604/65 |

FOREIGN PATENT DOCUMENTS

| | | |
|---|---|---|
| 0 148 319 | 7/1985 | European Pat. Off. |
| 0 462 422 | 12/1991 | European Pat. Off. |
| 0 472 480 | 2/1992 | European Pat. Off. |
| WO90/15631 | 12/1990 | WIPO |
| WO94/20158 | 9/1994 | WIPO |

OTHER PUBLICATIONS

Tobe et al, *High Efficiency Peritoneal Dialysis (HEPD): A New Method of Performing Peritonea Dialysis (PD)*, Peritoneal Dialysis International, XIVth Annual Conference on Peritoneal Dialysis Abstracts, vol. 14, Suppl. 1 (1994).

Longnecker et al, *Blood Loss During Maintenance Hemodialysis*, Trans. Amer. Soc. Artif. Int. Organs, vol. XX, 135–141 (1974).

Lewin et al, *Sorbent Based Regenerating Delivery System for Use in Peritoneal Dialysis*, Trans. Amer. Soc. Artif. Int. Organs, vol. XX, 130–134 (1974).

Raja et al, *Recirculation Peritoneal Dialysis with Sorbent Redy Cartridge*, Nephron 16: 134–142 (1976).

Warden et al, *The Use of Reciprocating Peritoneal Dialsysis with a Subcutaneous Peritoneal Catheter Peritoneal Catheter in End–Stage Renal Failure in Diabetes Mellitus*, Journal of Surgical Research 24, 495–500 (1978).

(List continued on next page.)

*Primary Examiner*—John Kim
*Attorney, Agent, or Firm*—Thomas S. Borecki; Charles R. Mattenson; Robert M. Barrett

[57] ABSTRACT

The present invention provides an improved peritoneal dialysis method and system. The system comprises a single catheter that is placed in the patient, a source of dialysate, and a diatyzer in fluid communication with the source of dialysate and the catheter. The system includes a single fluid pump in fluid communication with the source of dialysate and the catheter. The single pump is capable of pumping the dialysate into and out of the patient and back to the source of dialysate. The method includes the steps of placing a single catheter in a peritoneum of the patient, providing a source of dialysate, coupling the source of dialysate in fluid communication with the catheter on a single fluid circuit, pumping the dialysate from the source of dialysate into and out of the peritoneum using a single pump in the single fluid circuit.

20 Claims, 4 Drawing Sheets

OTHER PUBLICATIONS

Stephen, *Reciprocating Peritoneal Dialysis with a Sub cutaneous Peritoneal Catheter*, Dialysis & Transplantaton, vol. 7, No. 8, 834–838 (1978).

Mineshima et al, *Development of Continuous Recirculating Peritoneal Dialysis Using a Double Lumen Catheter*, ASAIO Journal, M377–M381 (1992).

Stephen et al, *Combined Technological–Clinical Approach to Wearable Dialysis*, Kidney International, Suppl. 8, vol. 13, S–125–S–132 (1978).

Gordon et al, *Augmentation of Efficiency by Continuous Flow Sorbent Regeneration Peritoneal Dialysis*, vol., XXII, Trans. Amer. Soc. Artif. Int. Organs, 599–604 (1976).

Lange et al, *Automatic Continuous High Flow Rate Peritoneal Dialysis*, vol. XIII, Trans Amer. Soc. Artif. Int. Organs, 164–167 (1967).

Miller et al, *Automated Peritoneal Dialysis: Analysis of Several Methods of Peritoneal Dialysis*, vol. XII, Amer. Soc. Artif. Int. Organs, 98–105 (1966).

Stephen et al, *Reciprocating Peritoneal Dialysis With a Subcutaneous Peritoneal Catheter*, Univ. of Utah, 32–35 (undated).

DiPaolo et al, *Acceleraton of Peritoneal Dialysis with Simple Device*, Nephron 19: 271–277 (1977).

Kablitz et al, *Technical Augmentation of Peritoneal Urea Clearance, Past, Present and Future*, Dialysis & Transplantation, vol. 9, No. 8, 741–744, 778 (1980).

Kablitz et al, *Reciprocating Peritoneal Dialysis*, Dialysis & Transplantation, vol. 7, 211–214 (1978).

Levitt et al, *Influence of Shaking on Peritoneal Transfer in Rats*, Kidney International, vol. 35, 1145–1150 (1989).

Stephen et al, *Recirculating Peritoneal Dialysis With Subcutaneous Catheter*, vol. XXII, Trans Amer. Soc. Artif. Int. Organs, 575–584 (1976).

ASAIO *Abstracts*, vol. 25th Annual Meeting, 48 (1979).

METHOD AND APPARATUS FOR PURIFIED PULSE PERITONEAL DIALYSIS USING A SINGLE PUMP

This application is a continuation of application Ser. No. 08/261,516, filed Jun. 17, 1994, now abandoned.

BACKGROUND OF THE INVENTION

The present invention relates generally to the treatment of end stage renal disease. More specifically, the present invention relates to methods and apparatus for performing peritoneal dialysis.

It is known to use dialysis to support a patient whose renal function has decreased to the point where the kidneys no longer sufficiently function. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semi-permeable membrane. The peritoneum is a membranous lining of the abdominal body cavity that due to a large number of blood vessels and capillaries is capable of acting as a natural semi-permeable membrane.

In continuous ambulatory peritoneal dialysis, a dialysis solution is introduced into the peritoneal cavity utilizing a catheter. Solutes (e.g., urea, creatinine etc.) diffuse from the blood into the dialysate due to the presence of a diffusion gradient. Similarly, the presence of an osmotic gradient between the peritoneal cavity and the blood causes fluid to be removed from the body into the dialysate which is then drained through the catheter. These processes allow the proper chemical and fluid balance to be returned to the body. After a sufficient period of time, an exchange of solutes between the dialysate and the blood is achieved. Fluid removal is achieved by providing a suitable osmotic gradient from the blood to the dialysate to permit water out flow from the blood. This allows the proper acid-base, electrolyte and fluid balance to be returned to the blood and the dialysis solution is simply drained from the body cavity through the catheter.

Peritoneal dialysis raises a number of issues including: the danger of peritonitis; a lower efficiency and therefore increased duration of dialysis hours compared to hemodialysis; and cost issues when automated equipment is utilized.

A number of variations on peritoneal dialysis have been explored. One such variation is reciprocating, recirculating, or semi-continuous peritoneal dialysis. In such systems, dialysis solution is infused into the peritoneal cavity and then, typically, on a continuous process basis a portion of the dialysis solution is sequentially drained, cleansed, and reinfused.

FIG. 1 illustrates early work performed by Shinaberger et al, in this area that is discussed in "Increasing Efficiency of Peritoneal Dialysis: Experience with Peritoneal-Extracorporeal Recirculation Dialysis", *Trans Amer Soc Artif Int Organs* 11 (1965): 76–82. As illustrated in FIG. 1, both an inflow 10 and outflow 12 catheter are utilized to produce a continuous single direction of dialysate flow. Sterile dialysate, which is purified by passage through a coil dialyzer 14 that is bathed in a 100 liter non-sterile dialysis bath, flows through the inflow catheter 10 and into the peritoneum. The dialysate then flows out of the peritoneum through the outflow catheter 12.

Further, work in this area in humans is disclosed in Stephen et al, "Recirculating Peritoneal Dialysis with Subcutaneous Catheter," *Transactions ASAIO* 22 (1976): 575–585. Gordon, A. et al, "Augmentation of Efficiency by Continuous Flow Sorbet Regeneration Peritoneal Dialysis", *Trans Amer Soc Artif Int Organs*, XXII (1976): 599–605, discloses further work in this area in dogs.

One disadvantage with the system of Shinaberger et al is that it requires the use of two catheters. Each catheter represents a separate exit site and possibility for infection.

Accordingly, one of the goals of further work in this area was the elimination of one of the catheters. Di Paolo in "Acceleration of Peritoneal Dialysis With Single Device", *Nephron*, 19: 271–277 (1977) discloses a single needle system. FIG. 2 illustrates the system of Di Paolo. A single needle 20 is used to infuse fluid from the sterile reservoirs 24, 26 into the patient where it dwells and then subsequently flows to drain 28. Inflow into the patient is achieved through a pump 30, while outflow is achieved by gravity.

U.S. Pat. No. 4,190,047 discloses a single catheter system that utilizes two pumps to alternate inflow and outflow of dialysate fluid. During the outflow cycle, fluid is passed through the blood path of the dialyzer where it is "cleaned" prior to the next in flow.

FIG. 3 sets forth a figure from U.S. Pat. No. 5,141,493. FIG. 3 illustrates the three loop system of the '493 patent wherein dialysate is reciprocated into and out of the patient using a reversible pump (first loop) into a second loop. In the second loop, the dialysate passes through a dialyzer being regenerated by non-sterile dialysate flowing in the third loop. The difference between this system and earlier systems is that both regeneration and reciprocation are continuous.

All of the above investigators have reported increased small molecule clearance and higher ultrafiltration with either a continuous flow or reciprocating type system. This is an advantage that is desirable. However, these systems are quite complex in their operation, set-up, and control. There is therefore a need for an improved peritoneal dialysis system based on a reciprocating, recirculating, or semi-continuous dialysis method.

SUMMARY OF THE INVENTION

The present invention provides an improved peritoneal dialysis method and system. The method utilizes a purified pulse peritoneal dialysis system.

To this end, a system for providing peritoneal dialysis to a patient is provided. The system comprises a single catheter that is placed in the patient, a source of dialysate, and a dialyzer in fluid communication with the source of dialysate and the catheter. A single sterile fluid pump is used for pumping the dialysate into and out of the patient.

In an embodiment, the system includes a force transducer coupled to the source of dialysate for monitoring the amount of dialysate present in the source of dialysate.

In an embodiment of the system, the pump is a reversible roller pump. In an embodiment of the system, however, the pump is a personal cycler (as defined hereinafter).

In an embodiment of the system, a pressure sensor can be placed in fluid communication with the pump.

The present invention also provides a method for dialyzing a patient. The method comprises the steps of: placing a single catheter in the peritoneal cavity of the patient; providing a source of dialysate; coupling the source of dialysate in fluid communication with the catheter, the dialysate passing through a dialyzer before reaching the catheter; and pumping the dialysate into and out of the peritoneum using a single pump.

Pursuant to the present invention, a dialysis method is provided wherein a double purification of fluid is provided. To this end, a single fluid circuit and pump is used. The fluid is purified when it is pumped into the peritoneal cavity and then when it is pumped from the cavity.

An advantage of the present invention is to provide an improved method for providing peritoneal dialysis to a patient.

A still further advantage of the present invention is to provide a purified pulse peritoneal dialysis system that requires only a single pump for sterile fluid.

Another advantage of the present invention is to provide a system that can be retro-fitted onto a standard dual stream proportioning system to provide an improved peritoneal dialysis method.

Furthermore, an advantage of the present invention is that it provides a system wherein the pulse of fluid is purified twice, once while going from the peritoneal cavity to the bag, and again, when returning to the peritoneal cavity from the bag.

Moreover, an advantage of the present invention is that it provides smaller stroke volumes allowing flow rates to be higher.

Still further, an advantage of the present invention is to provide for greater mixing by breaking up stagnant fluid layers in the peritoneal cavity.

Further, an advantage of the present invention is to provide a method wherein remaining fluid volume (bag plus peritoneal cavity) can be filtered toward the end of treatment to prevent protein loss from the patient.

Still further, an advantage of the present invention is that lower concentrations of glucose can be utilized as an osmotic agent since the glucose gradient is continually replenished. This will reduce the negative effects of high glucose concentrations on the peritoneal membrane.

Further, an advantage of the present system is that nutritional and other additive substances for the benefit of the patient can be added to the dialysate in a nonsterile form thus reducing the cost of those additives.

Finally, an advantage of the present system is that smaller quantities of sterile fluid are utilized than are required in other therapies such as CAPD resulting in substantial cost savings.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides improved methods and systems for providing peritoneal dialysis to a patient. Specifically, the present invention provides a purified pulse peritoneal dialysis system. Pursuant to the system of the present invention, a single pump for sterile fluid, as well as a single catheter, can be utilized.

Figure 4:
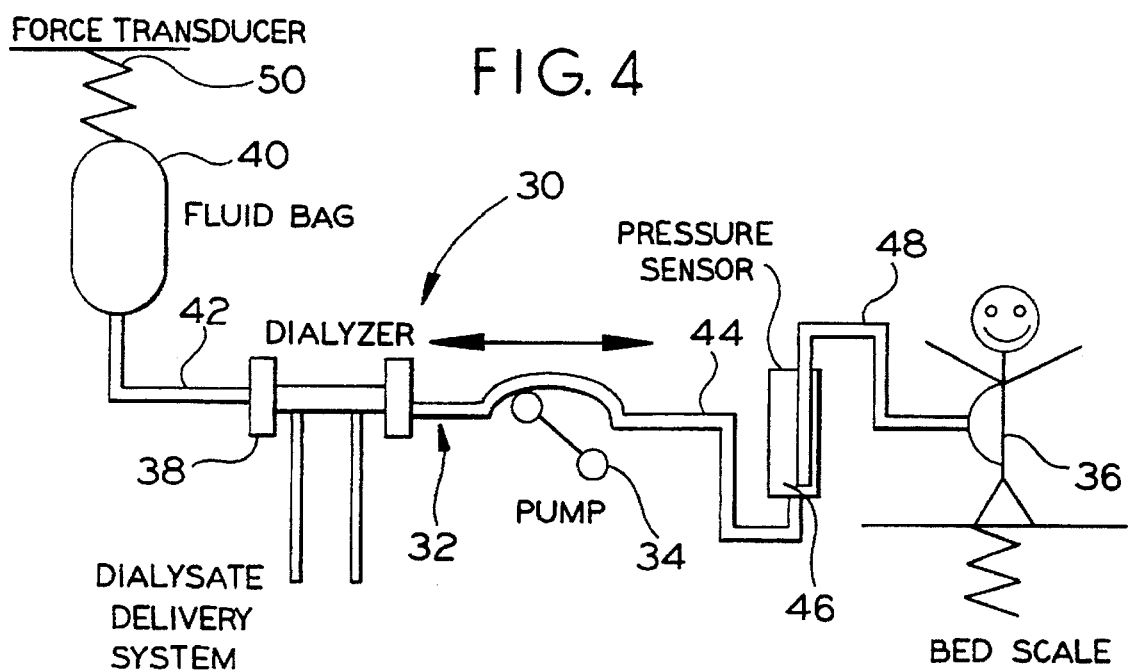
FIG. 4 illustrates, schematically, an embodiment of the system of the present invention.

Referring now to FIG. 4, as illustrated, the present invention provides a system 30 including a sterile fluid circuit 32 and a single pump 34 that is used to pulse fluid into and out of the peritoneal cavity of the patient 36. Unlike the prior art methods which required multiple pumps and circuits which resulted in complicated systems which are difficult to set up and expensive, the present invention provides a single sterile fluid circuit that requires only a single pump.

As illustrated and discussed in detail below, pursuant to the present invention, reciprocation is directly through the dialyzer 38 such that both cocurrent and countercurrent removal takes place. This results in a number of advantages.

One advantage is that the same pulse of fluid is purified twice—once while going from the peritoneal cavity to the peritoneal dialysis bag; and again, when returning to the peritoneal cavity from the bag. By providing double purification, a smaller surface area dialyzer can be used than would be necessary if a single pass mode (such as in the prior art methods) were utilized. For example, a dialyzer 38 such as a Baxter CA70 pediatric dialyzer can be used.

In the embodiment of the system 30 illustrated in FIG. 4, a bag 40 of dialysate is provided. The dialysate can be any peritoneal dialysis solution desired. The dialysate is in fluid communication with the dialyzer 38 by a fluid line 42.

Fluid (dialysate) is moved through the dialyzer 38 in both directions as it is pumped into and out of the patient 36 by use of the single pump 34. In the embodiment illustrated, the pump is a reversible roller pump 34. The pump 34 is positioned to act on a fluid line 44 that extends from an end of dialyzer 38 to a pressure sensor 46. A further fluid line 48 extends from the pressure sensor 46 to the patient 36. A number of fluid pressure sensors can be used, such as, for example, a Cole-Palmer G-68801-53 diaphragm-type pressure sensor.

Fluid line 48 terminates at a catheter that is in fluid communication with the peritoneal cavity of the patient 36. The pump 34 can cause fluid to move in either direction through the fluid circuit of the system 30.

Pursuant to the present invention, by use of the pump 34, the fluid (dialysate) can be transported via small stroke volumes. By way of example, these small stroke volumes can be roughly two to three times the dead space of the tubing, of fluid line 44, and dialyzer 38 and less than 15% of the total fill volume. This will allow fluid to be moved at high flow rates (400 ml/min) both into and out of the patient without injuring the peritoneum. This provides, among other things, for a greater mixing in the peritoneal cavity by breaking up stagnant fluid layers in the cavity.

In the embodiment illustrated in FIG. 4, the amount of fluid that is pumped is measured by a force transducer 50. In the embodiment illustrated in FIG. 4, the fluid bag 40 is hung from the force transducer 50. An example of such a force transducer is an Omega LCB-50 Bending Beam Load Cell. As discussed below, with reference to FIG. 7, a force transducer is not required for certain embodiments of the present invention. Likewise, in certain embodiments a pressure sensor 46 is not required.

Figure 7:
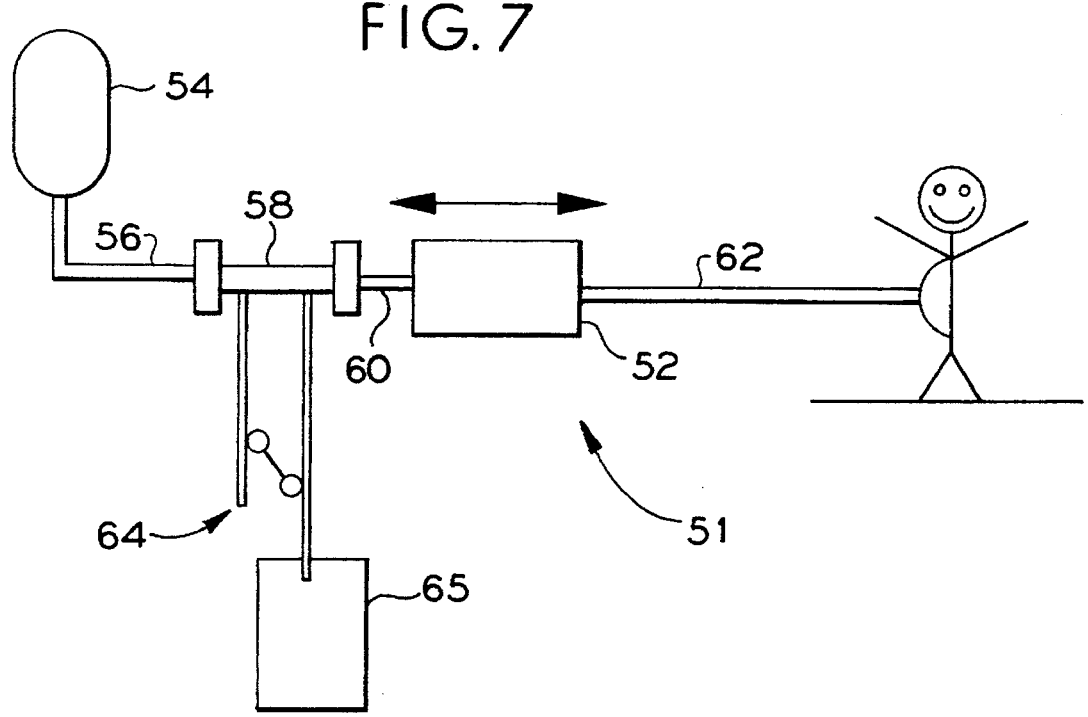
FIG. 7 illustrates, schematically, another embodiment of the system of the present invention.

Because fluid may be lost from the system 30 via ultrafiltration across the dialyzer membrane, it is desirable, pursuant to the embodiment illustrated in FIG. 4, to periodically weigh the patient via a bed scale, although in certain embodiments of the invention as shown in FIG. 7 use of the bed scale is not required. Fluid can then be added or subtracted from the peritoneal cavity by moving it into and out of the hanging fluid bag 40 to compensate for dialyzer ultrafiltration loss. Additionally, ultrafiltration generated by the osmotic gradient between the blood and peritoneal cavity (due to high glucose concentration) can also be removed in this manner.

The dialysate delivery system 30 can be used with a standard dual stream proportioning device such as the Baxter SPS 550 or SPS 1550. Glucose can be metered at different concentrations by having one pump adjustable to different dilution ratios. In the SPS 550 or 1550 devices, this could be accomplished by placing all the glucose in the B concentration and all the electrolytes in the A concentrate. A similar effect could also be obtained by using concentrates with different fixed glucose concentrations. Temperature or conductivity alarms sensed by the dialysate delivery system will stop the reciprocating pump until the correct condition of dialysate fluid is restored. Similarly, a pressure alarm will also shut off the pump. A standard dual stream proportioning scheme can be used to obtain the non-sterile dialysate on the dialysate side of the dialyzer. Variable glucose proportioning can be obtained by using a variable proportioning bicarbonate pump.

Figure 6:
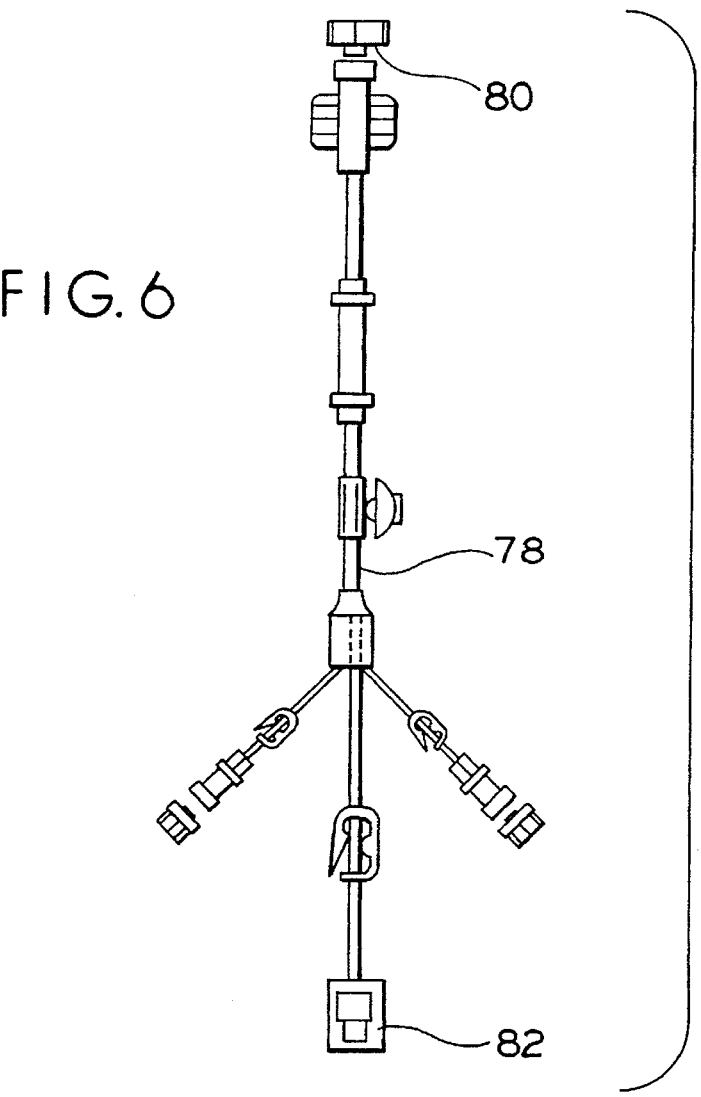
FIG. 6 illustrates a perspective view of another set that can be used in the present invention.

Pursuant to the present invention, standard bags of sterile dialysis can be used to prime the circuit. This eliminates the need for a fluid sterilizing chamber. To prime the system, the following procedure can be followed:

A sterile connection is made between a sterile source bag of fluid (preferably 3000 ml or greater) and the sterile line set with dialyzer. The line set 70 consists of (1) a piece of sterile tubing 72 with a spike 74 on one end to fit into a bag and a luer lock 76 on the other to fit into the dialyzer (see FIG. 5), (2) a standard "tight membrane" pediatric dialyzer (e/g/, Baxter CA50 or CA70), and (3) a longer line 78 consisting of a luer lock 80 on one end to fit to the dialyzer and a patient connector 82 on the other end to hook to the patient's transfer set, when using a roller pump that fits into the reversible roller pump (see FIG. 6).

The system may also include provisions for line pressure monitoring. In the process described below, this was a 'drip bulb' where there is an air and water interface. The air interface connects to a pressure transducer through a 0.22µ membrane (which excludes viruses and bacteria). Both line sets 70 and 78 have plastic clamps to stop and start flow.

The upper clamp between the bag and line set 70 is opened as well as the lower clamp between the patient connection and dialyzer. About 250 ml of fluid flows through the dialyzer and line set and is discarded.

Nonsterile dialysate is placed on the dialysate side of the dialyzer. The dialyzer is inverted and bubbles are removed from the system.

The lower clamp is closed, the bag is raised and fluid crosses the dialyzer membrane to the nonsterile side. The speed of this transport can be increased by increasing the pressure difference between the sterile and nonsterile sides of the dialysate membrane. About 300 ml of fluid are allowed to cross the membrane. If the dialyzer is gamma sterilized, however, this procedure may be omitted.

After this procedure is completed, the line set 70 is connected to the patient who is then filled with dialysate.

Pursuant to the present invention, toward the end of the treatment the remaining volume (bag plus peritoneal cavity) can be filtered if desired. By filtering the remaining volume one can prevent protein loss.

Referring now to FIG. 7, another embodiment of the present invention is illustrated. In this embodiment, of the system 51, rather than utilizing a reversible roller pump, as used in the embodiment of the invention illustrated in FIG. 4, a "personal cycler" 52 can be used.

"Personal cycler", as that term is used in the present application, refers to a pressure driven, diaphragm-type volumetric displacement pump. The personal cycler 52 can determine the volume of liquid delivered as the difference in the volume of a pumping chamber before and after a pumping stroke. The pumping chamber consists of two parts separated by a flexible diaphragm with air on one side and fluid on the other. Increasing the air pressure pushes liquid out of the chamber expanding the volume on the air side.

The personal cycler 52 measures the pressure on the air side of the diaphragm and the pressure in a known standard volume before and after the pumping chamber is connected to the standard volume. Based on these measurements, the personal cycler 52 can determine the amount of fluid delivered. The formula for such measurements is as follows:

$$V_{delivered} = V_{filled} - V_{empty} = [(P_{s1} - P_{s2}) * V_s/(P_{d2} - P_{d1}]_{filled} - [P_{s1} - P_{s2}) * V_s/(P_{d2} - P_{d1}]_{empty}$$

where "1" refers to the pressure before the air side of the diaphragm is connected to the standard volume where "2" refers to the pressure after the aid side of the diaphragm is connected to the standard volume "s" refers to the standard volume "d" refers to the air side of diaphragm.

Examples of a personal cycler are disclosed in U.S. applications: "Peritoneal Dialysis Systems and Methods Employing a Liquid Distribution and Pumping Cassette That Emulates Gravity Flow", filed Mar. 3, 1993, Ser. No. 08/027,328; "Peritoneal Dialysis Systems and Methods Employing a Liquid Distribution and Pump Cassette with Self-Contained Air Isolation and Venting", filed Mar. 3, 1993, Ser. No. 08/027,484; "Liquid Pumping Mechanisms for Peritoneal Dialysis Systems Employing Fluid Pressure", filed Mar. 3, 1993, Ser. No 08/027,485; "Peritoneal Dialysis Systems and Methods Employing Pneumatic Pressure and Temperature-Corrected Liquid Volume Measurements", filed Mar. 3, 1993, Ser. No. 08/026,458; "Improved User Interface and Monitoring Functions for Automated Peritoneal Dialysis Systems", filed Mar. 3, 1993, Ser. No. 08/025,531; "Improved User Interface for Automated Peritoneal Dialysis Systems", filed Mar. 3 1993, Ser. No 08/025,547; and "Peritoneal Dialysis Cycler", filed Mar. 3, 1993, Ser. No. 08/006,426, the disclosures of all of which are incorporated herein by reference.

Accordingly, pursuant to this embodiment of the invention, dialysate is provided by a fluid bag 54. Fluid (dialysate) flow is through fluid line 56 through a dialyzer 58. Fluid line 60 connects an end of the dialyzer 58 with the personal cycler 52. A second end of the personal cycler 52 is coupled to the patient 36 by fluid line 62 that terminates at a catheter in fluid communication with the patient's peritoneal cavity.

A personal cycler 52 affords fluid flow into and out of the patient. Similar to the pump of FIG. 4, the personal cycler 52 allows fluid flow in either direction of the fluid circuit. Because the personal cycler is a pressure driven volume displacement pump, fluid can be precisely metered without an external load sensor being required. Moreover, since line pressure is precisely known, this number can be fed back to the dialysis machine so that the transmembrane pressure (TMP) can be adjusted so that no fluid leaves the system.

An advantage of the system illustrated in FIG. 7 is that the patient need not be weighed during the process. Further, because pressure is directly sensed by the personal cycler, safety pressure sensors, utilized in the embodiment illustrated in FIG. 4, are not required.

Figure 5:
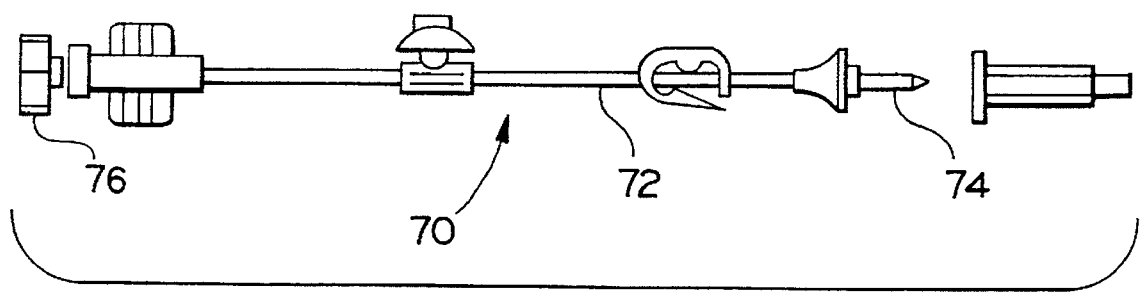
FIG. 5 illustrates a perspective view of a set that can be used in the present invention.

Still further, the dialysate delivery system illustrated in FIG. 5 does not have to be restricted to a dual stream proportioning device. Rather, the system could consist of a batch system 65 where dialysate powder could be mixed with a source of pure water. This resulting mixture could be metered at a slower rate by a double threaded peristaltic pump 64 or a set of infusion pumps with matched pumping rates. The double threading or matching of pumping rates eliminates ultrafiltration across the dialyzer membrane which arises due to transmembrane pressure. Preferably, the peristaltic pump is three headed rather than two headed so that total occlusion is always maintained as the pump rotates.

In a further embodiment, not illustrated, rather than utilizing a personal cycler, a reversible stepper motor pump could be used. This would allow fluid to be metered precisely with an external load sensor. However, because the reversible stepper motor pump is a roller pump, in-line pressure sensor would preferably be used for patient's safety.

By way of example, and not limitation, an example of the present invention will now be given:

EXAMPLE NO. 1

Figure 1:
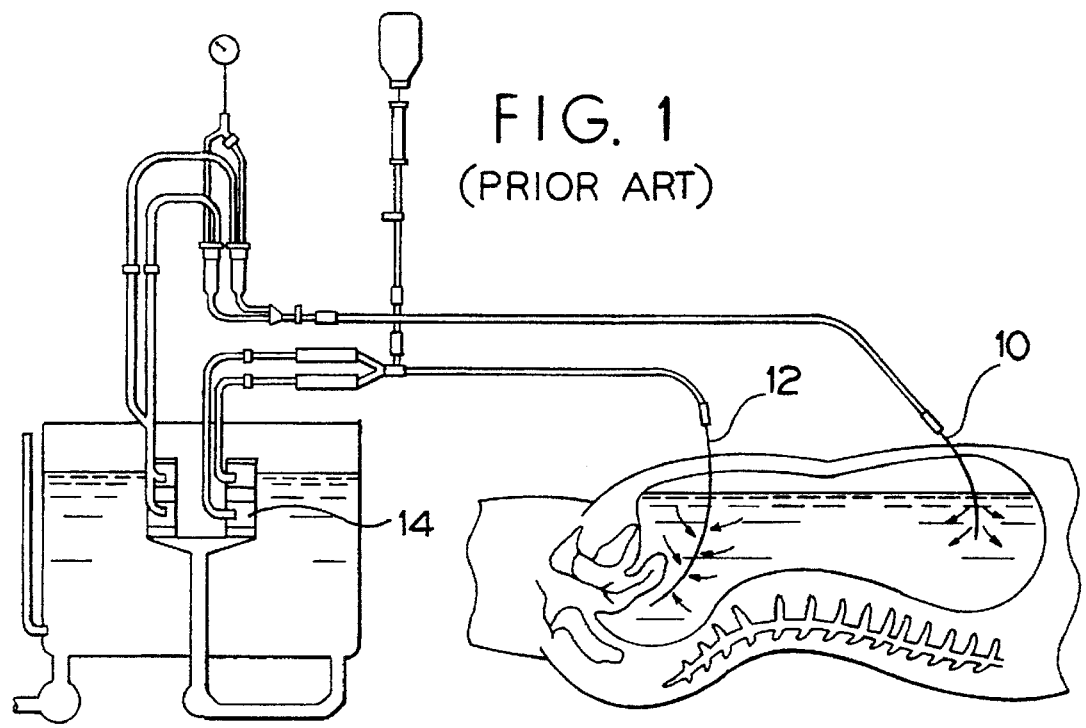
FIG. 1 illustrates, schematically, a prior art peritoneal dialysis method.
Figure 2:
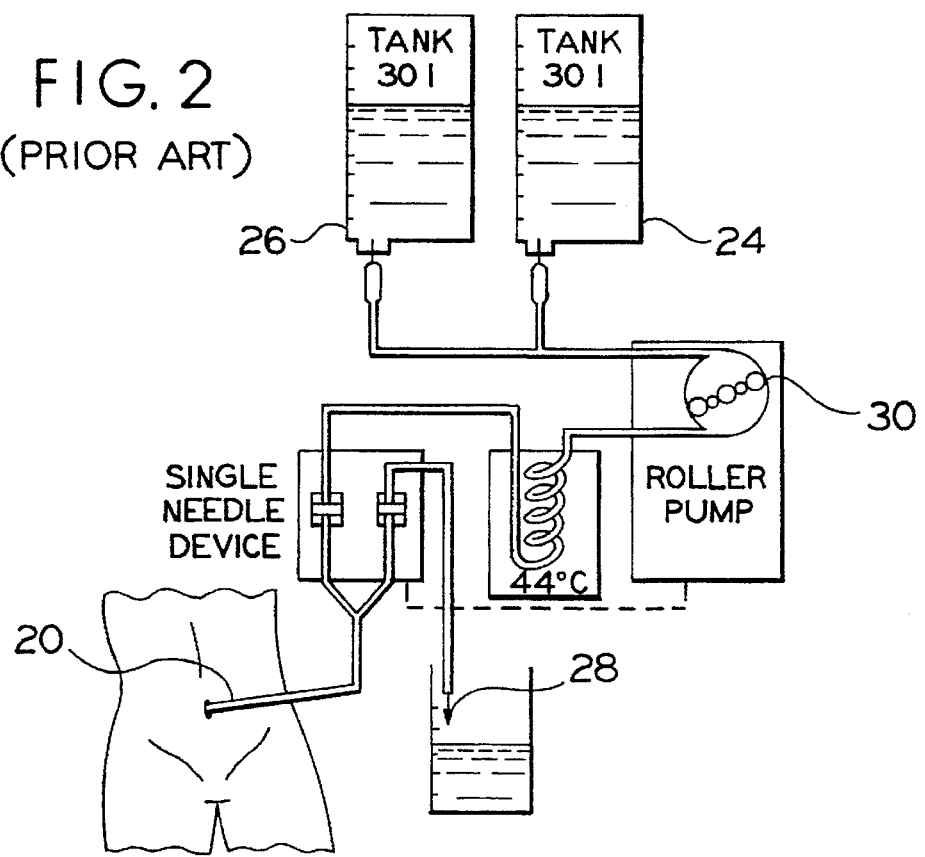
FIG. 2 illustrates, schematically, another prior art peritoneal dialysis method.
Figure 3:
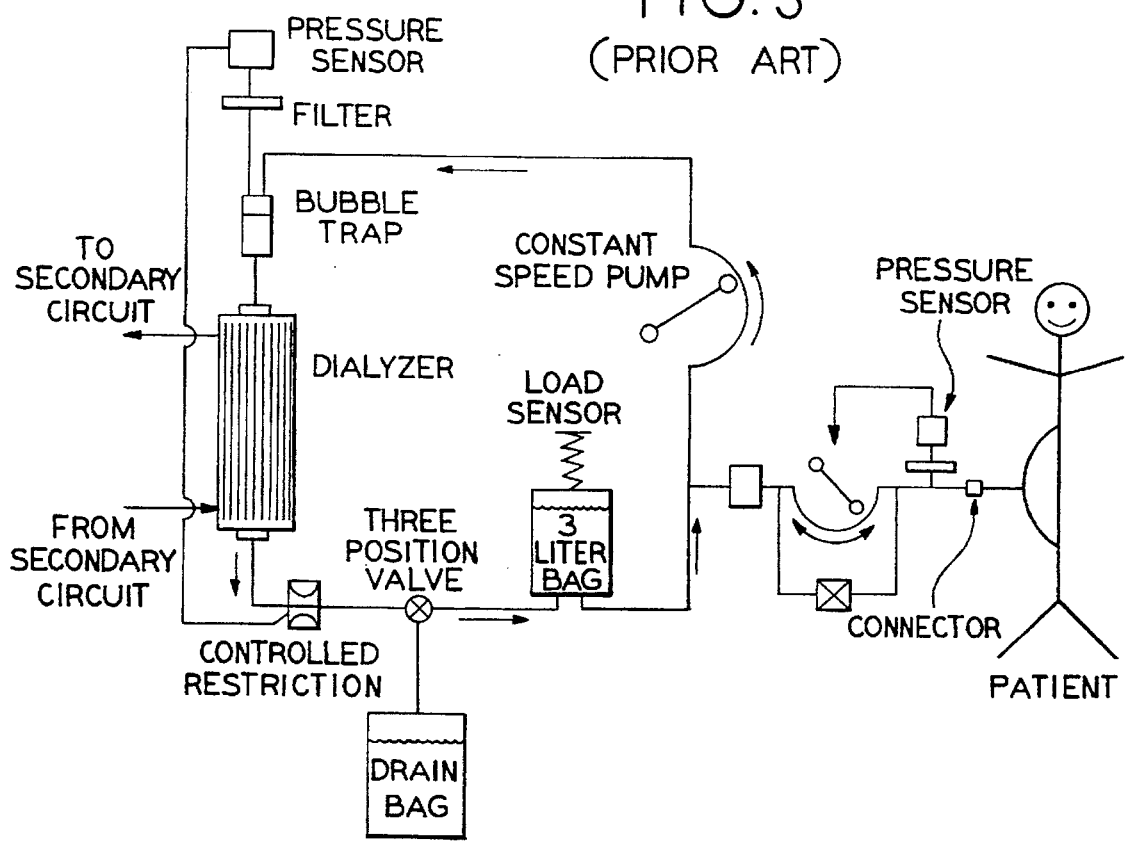
FIG. 3 illustrates, schematically, a still further prior art peritoneal dialysis method.
Figure 8:
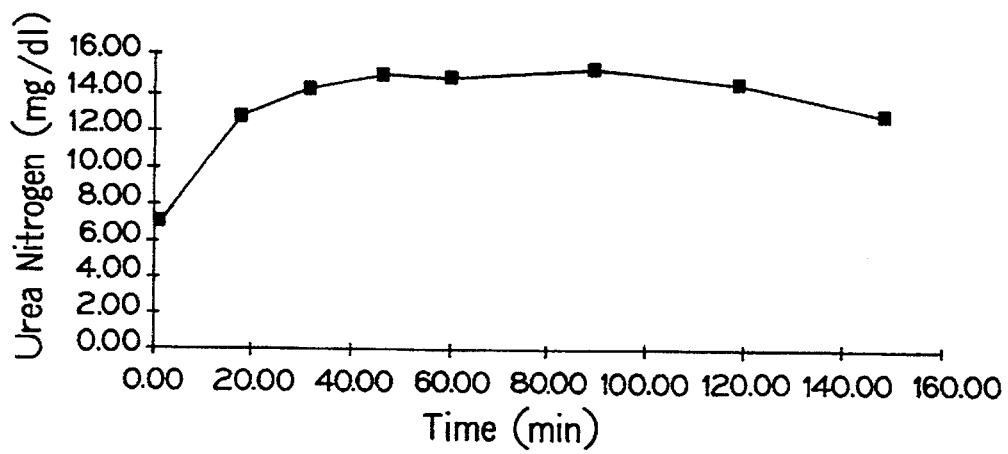
FIG. 8 illustrates a typical concentration time profile for a PPPD system.

Four patients were run on the system of the present invention illustrated in FIG. 4 ("PPPD"). After the patient was filled with 2 liters of fluid (1.5l in the case of #11), fluid was pumped from the external bag into and out of the patient cavity in 300 ml strokes through a CA70 cellulose acetate dialyzer for a period of 150–180 minutes. Average intraperitoneal volume varied from 1700 ml+the residual volume to 2000 ml+the residual volume during this time period. Waste dialysate was collected from the back of the dialysis machine into a large tank. Samples were taken through a 0.22μ filter from a "T" in the line set at periodic intervals both when the flow was leaving the peritoneal cavity and when the flow was entering the peritoneal cavity. FIG. 8 illustrates the typical cavity concentration as a function of time. Unlike continuous ambulatory peritoneal dialysis where concentration continues to increase, the cavity concentration reaches a steady value (about 14 ml in the figure) and then declines as the total body concentration of the solute (urea) decreases. The diffusion gradients are thus maintained so that maximum solute transport occurs.

For reference, a 90 minute PET exchange was performed using a "Y" set with an attached drain bag immediately before and immediately after the PPPD exchange described above. After instilling 2 liters of 2.5% Dianneal® samples were taken every 15–30 minutes during this exchange by draining 200 ml of fluid from the cavity and mixing. After the sample was taken, the fluid was again reinfused. After 90 minutes, the patient was drained and the quantity of fluid was measured and a sample was taken from the drain bag.

Augmentations for this therapy were calculated as the average clearance of the two PET exchanges (representing one cycle of typical nighttime therapy ("NPD")) divided by the total clearance of the PPPD exchange and are shown in the following table in the leftmost columns. These augmentations represent a higher estimate of those achievable insofar as the total removal is comprised of the amount of solute removed via the purification process, as well as the amount remaining in the patient's cavity and the external bag at the end of the treatment. Over eight hours or more, these latter amounts will be less in proportion to the amount removed by the purification process. The more typical augmentations over 8–10 hours are shown in the two rightmost columns of Table 1. These were computed as the steady state PPPD clearance (rather than the total clearance) divided by the average of the PET clearances. Table 2 shows the typical achievable clearances in liters/week for 7 ten hour treatments using a worst case clearance analysis. In practice when cycling between 2000 ml and 2300 ml (rather than 1700 ml and 2000 ml) and adding in the effect of removal to the cavity and the external bag, these clearances should average 20% higher.

TABLE 1

Percent increase of PPPD efficiency over NPD.

|  | Urea Aug | Crtn Aug | Urea Aug | Crtn Aug |
| --- | --- | --- | --- | --- |
| #1 | 82.15 | 54.78 | 34.98 | 19.97 |
| #3 | 49.49 | 30.37 | 46.58 | 25.56 |
| #4 | 28.58 | 7.05 | 20.11 | 3.22 |
| #11 | 23.08 | −7.72 | 44.81 | 29.48 |
| Avg | 45.83 | 21.12 | 36.62 | 19.56 |

TABLE 2

Liters per week of clearance (worst case analysis) for 600 minutes of nightly PPPD therapy both with wet and dry days. Residual renal function is neglected.

|  | Dry Urea | Dry Crtn | Wet Urea | Wet Crtn |
| --- | --- | --- | --- | --- |
| #1 | 68.42 | 41.17 | 78.42 | 51.17 |
| #3 | 75.29 | 43.41 | 85.29 | 53.41 |
| #4 | 61.38 | 28.17 | 71.38 | 38.17 |
| #11 | 58.18 | 38.34 | 68.18 | 48.34 |
| Avg | 65.82 | 37.77 | 75.82 | 47.77 |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A system including only one pump for providing peritoneal dialysis to a patient comprising:

a single catheter that is placed in the patient and is coupled to an end of a first fluid line of a single fluid circuit;

a source of dialysate that is coupled to an end of a second fluid line of the single fluid circuit;

a dialyzer that is in fluid communication with the first and second fluid lines and thereby with the source of dialysate and the catheter; and a single pump positioned in the single fluid circuit between the source of dialysate and the single catheter and comprising the only means for pumping the dialysate from the source of dialysate into and out of the patient, through the dialyzer and back to the source of dialysate.

2. The system of claim 1 including a force transducer coupled to the source of dialysate for monitoring the amount of dialysate present.

3. The system of claim 1 wherein the pump is a reversible roller pump.

4. The system of claim 1 including a pressure sensor in fluid communication with the pump.

5. The system of claim 1 wherein the pump is a personal cycler.

6. A method for dialyzing a patient comprising the steps of:

placing a single catheter in a peritoneum of the patient;

providing a source of dialysate;

coupling the source of dialysate in fluid communication with the catheter on a single fluid circuit, the dialysate passing from the source of dialysate through a dialyzer to be dialyzed before reaching the catheter; and pumping the dialysate in the single fluid circuit from the source of dialysate into and out of the peritoneum and through the dialyzer using a single pump.

7. The method of claim 6 including coupling the source of dialysate to a force transducer for monitoring the amount of dialysate present.

8. The method of claim 6 including the step of using as the pump a reversible roller pump.

9. The method of claim 6 including placing a pressure sensor in fluid communication with the pump.

10. The method of claim 6 wherein the dialysate is purified twice, once when passing from the source of dialysate through the dialyzer to the patient, and once when being pumped out of the peritoneum through the dialyzer to the source of dialysate.

11. The method of claim 6 including the step of coupling the source of dialysate to a personal cycler for pumping the dialysate.

12. The method of claim 6 including the step of using a pressure sensor to monitor the pressure in the single fluid circuit.

13. The method of claim 6 including the step of using a dual proportioning system to provide non-sterile dialysate.

14. The method of claim 6 including the step of using a single double threaded peristaltic pump to pump non-sterile dialysate.

15. A method for dialyzing a patient comprising the steps of:

placing a single catheter in a patient;

coupling the catheter to a source of dialysate using a single fluid circuit;

placing in the single fluid circuit a dialyzer;

providing and positioning a single pump in the single fluid circuit to pump dialysate from the source of dialysate into and out of the patient; and causing the dialysate to flow through the dialyzer as it is pumped with the single pump into the patient from the source of dialysate; and when it is pumped out of the patient to the source of dialysate.

16. The method of claim 15 including coupling the source of dialysate to a force transducer for monitoring the amount of dialysate present.

17. The method of claim 15 including the step of using as the pump a reversible roller pump.

18. The method of claim 15 including placing a pressure sensor in fluid communication with the pump.

19. The method of claim 15 including the step of coupling the source of dialysate to a personal cycler for pumping the dialysate.

20. The method of claim 15 including the step of using a pressure sensor to monitor the pressure in the single fluid circuit.

* * * * *

UNITED STATES PATENT AND TRADEMARK OFFICE
CERTIFICATE OF CORRECTION

PATENT NO. : 5,641,405
DATED : June 24, 1997
INVENTOR(S) : Prakash Keshaviah, et al It is certified that error appears in the above-identified patent and that said Letters Patent is hereby corrected as shown below:

In the Abstract: line 4, please delete "diatyzer" and insert --dialyzer--.

Signed and Sealed this

Ninth Day of December, 1997

Attest:

BRUCE LEHMAN

Attesting Officer

Commissioner of Patents and Trademarks